United States Patent [19]
Pinsky et al.

[11] Patent Number: 5,315,122
[45] Date of Patent: May 24, 1994

[54] APPARATUS AND METHOD FOR FLUORESCENT LIFETIME MEASUREMENT

[75] Inventors: Bertram G. Pinsky, Hayward; John J. Ladasky, Jr., San Jose, both of Calif.

[73] Assignee: Becton, Dickinson and Company, Franklin Lakes, N.J.

[21] Appl. No.: 935,486

[22] Filed: Aug. 25, 1992

[51] Int. Cl.$^5$ ............................................. G01N 21/64
[52] U.S. Cl. ................................. 250/461.2; 250/459.1; 356/318
[58] Field of Search ............... 250/461.2, 458.1, 459.1; 356/318, 417; 436/172

[56] References Cited

U.S. PATENT DOCUMENTS

| | | | |
|---|---|---|---|
| 3,855,930 | 8/1989 | Chao et al. | 364/497 |
| 4,058,732 | 11/1977 | Wieder | 250/461 B |
| 4,198,567 | 4/1980 | Eneroth et al. | 250/459 |
| 4,778,593 | 10/1988 | Yamashita et al. | 250/461.2 |
| 4,910,467 | 3/1990 | Leitch | 329/306 |

OTHER PUBLICATIONS

Spencer et al, "Fluorescence Lifetimes" Annals of the NY Academy of Sciences p. 361 (1969).
"Microwave Systems Designer Handbook," Jul., 1987, vol. 17, p. 155.
"Radio Concepts," Ralph S. Carson, pp. 279–282.
Spencer, Richard Dale, 1942. Fluorescence Lifetimes: Theory, Instrumentation, and Application of Nanosecond Fluorometry. University of Illinois at Urbana--Champaign, Ph.D., 1970.
Spencer, Richard D. and Weber, Gregorio. Measurements of Subnanosecond Fluorescence Lifetimes with a Cross-Correlation Phase Fluorometer. University of Illinois at Urbana, Ill.
Berndt et al., "Phase-Modulation Fluorometry Using a Frequency-Doubled Pulsed Laser Diode Light Source," Rev. Sci. Instrum., 61(7), p. 1816 (1990).
Vo-Dinh et al., "Phase-Resolved Fiber-Optics Fluoroimmunosensor," Applied Spectroscopy, 44(1), p. 128 (Jan. 1990).

Primary Examiner—Paul M. Dzierzynski
Assistant Examiner—Richard Hanig
Attorney, Agent, or Firm—Michael G. Schwarz

[57] ABSTRACT

A flow cytometer measures fluorescence lifetimes by the phase shift of a reference signal and an emission from a fluorescent particle or cell in a flow chamber in order to identify the particle or cell. An acoustic optic modulator modulates laser light with a sinusoidal wave of a predetermined frequency to excite particles or cells. Detectors respond to emissions of individual particles or cells in the form of an output signal pulse at the predetermined frequency. Signals representative of fluorescence emitted and reference beam signals is measured. The particle is identified by the phase shift.

15 Claims, 4 Drawing Sheets

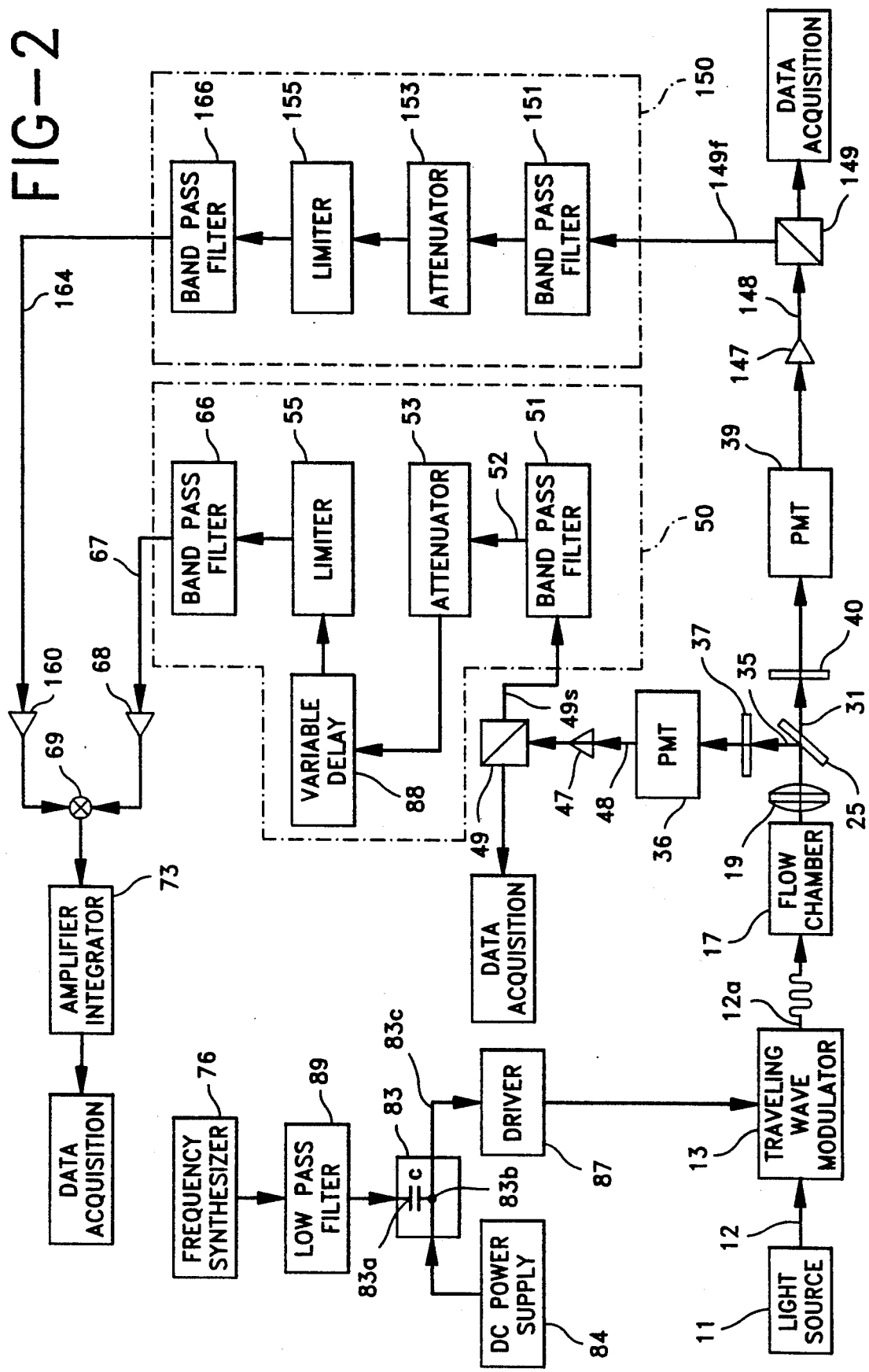

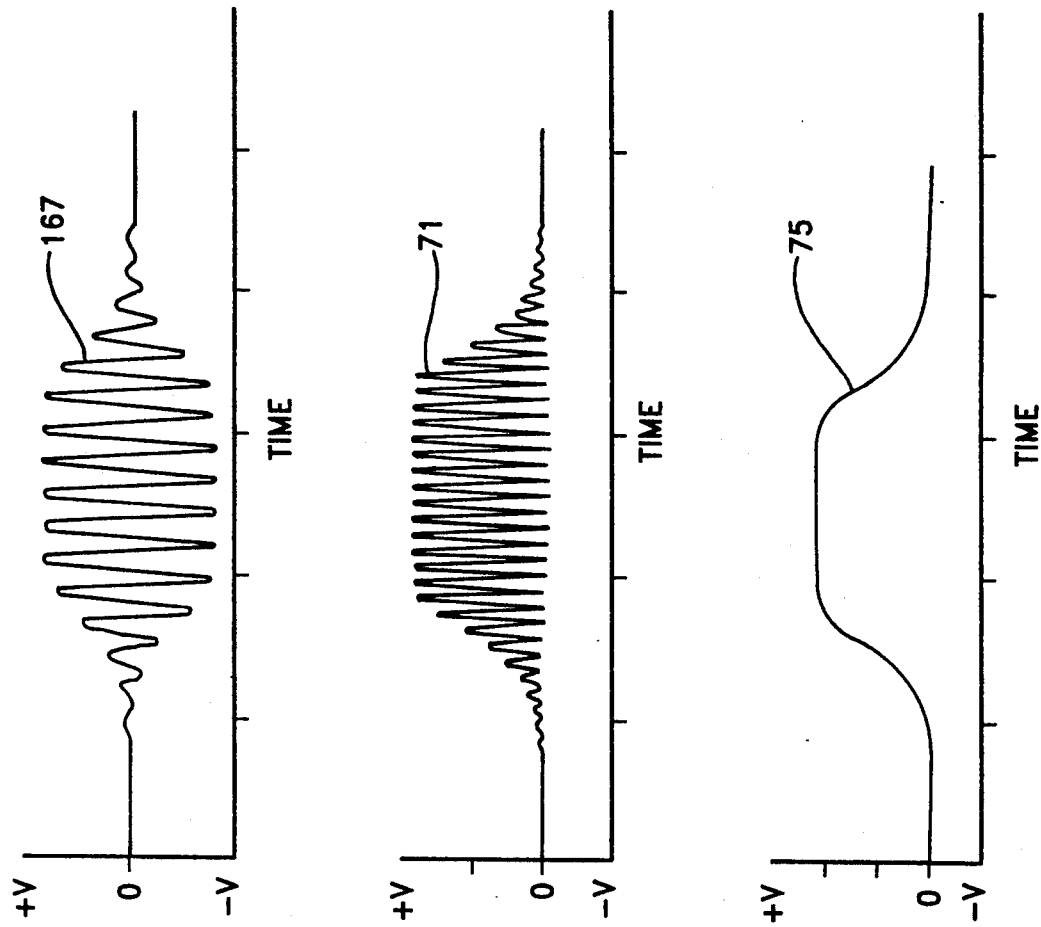

APPARATUS AND METHOD FOR FLUORESCENT LIFETIME MEASUREMENT

FIELD OF THE INVENTION

This invention generally relates to the field of flow cytometry. Specifically, it relates to the excitation of stained cells or particles with modulated laser light to obtain fluorescent emissions in order to identify the cells or particles by measuring the phase shift of the fluorescent emissions relative to a reference.

BACKGROUND

In a flow cytometer, cells or particles tagged with markers or dyes are passed through a light beam at relatively high speed. Typically the identity of the cells or particles is determined by measuring the intensity of fluorescent emissions produced by the cells or particles or the intensity of the light scattered by the cells or particles. However, intensity measurements alone may not be adequate to identify particles. For example, the resolution of multiple signals with similar emission spectra and similar intensities, suppression of a single emitted signal from multiple signals of similar intensities, and normalization of intensity varying signals with the same or different fluorescent lifetimes are not possible using intensity measurements alone. In general, fluorescent lifetime or phase shift cannot readily be measured by intensity measurements alone.

Fluorescently tagged particles may have multiple fluorescent tags, some having similar emission spectra. Previously the only way to separate these signals with similar emissions was through differences in intensities between light emitted by cells of different types when illuminated. If the signals had similar intensities then the multiple signals could not be resolved. In contrast, the present invention allows such signals to be resolved even if they have different lifetimes and the same or different intensities.

Fluorescent lifetime is associated with the radiative transition from a fluorescent agent's excited state to its relaxed state. The excited state is dependent on the nature of the fluorescent agent. The fluorescent agent (fluorochrome) is chosen to be, or is a natural property of, the cell or particle under observation. The lifetime of the fluorescent agent may be determined by phase sensitive or modulation sensitive techniques.

The fluorescent lifetime of a cell, $\tau$, is dependent on the phase shift of the fluorescent emission relative to a reference signal as follows:

$$\tau = 1/\omega(\tan\theta)$$

where $\omega = 2\pi f$, $f$ = frequency of the excitation beam $\theta$ = phase angle (shift) between the fluorescent emission and the excitation beam The fluorescent lifetime may also be determined from the depth of modulation factor m.

$$\tau = 1/\omega(1/m^2 - 1)^{1/2}$$

Fluorescent lifetime may thus be resolved through the measurement of the phase shift "$\theta$" between the fluorescent emission and the excitation light beam. The measured signal may include multiple lifetime signals, and therefore multiple phase signals.

While the detection of phase shift between signals is known, an apparatus and method for determination of phase fluorescence in a high speed and therefore dynamic system is not well known. Determination of the phase shift between a modulated wave and the modulated emission from the cell or particle in a flow cytometer is problematic because of the high speed at which each cell or particle passes through the flow chamber and the widely varying intensity of the signal resulting from emissions of fluorescence.

Since the phase measurement is a relative measurement, the choice of the reference from which the measurement is taken is important.

In order to obtain a reference against which the phase measurement may be taken, the intensity of the excitation light beam is modulated. An acoustic optic modulator is used to modulate the illuminating light beam. The acoustic optic modulator may be a traveling wave modulator or a standing wave modulator. It is desirable to use a traveling wave modulator rather than a standing wave modulator to modulate the illuminating light beam for several reasons including: a traveling wave modulator is cheaper than a standing wave modulator; a traveling wave modulator is able to produce a wider range of modulating frequencies than a standing wave modulator and the efficiency of a traveling wave modulator is greater than that of a standing wave modulator over a range of frequencies.

A standing wave modulator produces modulated waves, which, when viewed from a point directly in the path of the modulated light beam, have constant phase. That is to say, the beam is made up of waves whose phase is constant across any cross section through the beam which is perpendicular to the direction of propagation of the waves. In contrast, a traveling wave modulator produces a beam comprising waves whose phase is not constant across a perpendicular cross section of the beam.

A method and apparatus for detecting phase fluorescence is disclosed in copending U.S. Pat. application No. 07/705,044, now abandoned assigned to Becton, Dickinson and Company and which is incorporated herein by reference. In that application, the modulator is a standing wave modulator. The modulating frequency is provided by a frequency synthesizer which also provides the reference against which the phase fluorescence is measured.

When a traveling wave modulator is used, the use of the signal from the frequency synthesizer as a reference poses difficulties. This is because the phase of the modulated waves varies transversely across the light beam. Since the positions of particles in a flow cytometer may vary, causing them to intersect different parts of the illuminating light beam, the phase of the fluorescent light varies with the positions of the particles.

SUMMARY OF THE INVENTION

The present invention uses the fact that when a fluorescently tagged particle is illuminated, fluorescence is emitted and light is also scattered by the particle. The scattered light, which has the same phase as the incident light at the position of the particle is used as a reference from which to determine the phase shift in the fluorescent light. Alternately, if the particle emits a second fluorescence signal of a different color than the fluorescence signal of interest, that second fluorescence signal may be used as a reference. The difference in phase that is a consequence of the position of the particle in the light beam is thus rendered immaterial.

BRIEF DESCRIPTION OF THE DRAWINGS

FIG. 2 is a block diagram of the invention;

FIG. 3a–f are diagrams of the waveforms at various stages of analysis in the invention.

DETAILED DESCRIPTION

Figure 1:
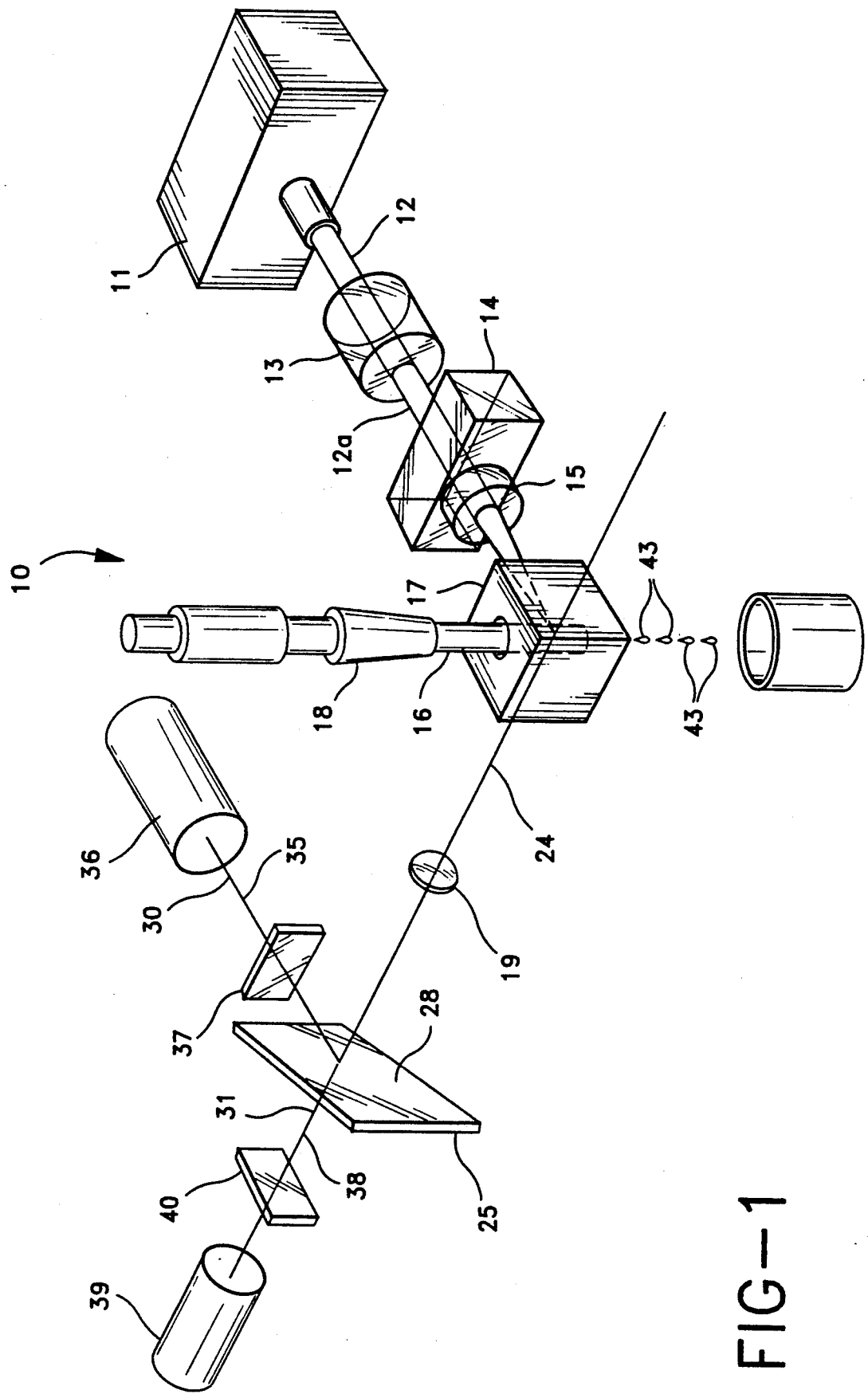
FIG. 1 is a perspective view of the basic components of a flow cytometer incorporated in the present invention.

While this invention is satisfied by embodiments in many different forms, a preferred embodiment of the invention is shown in the drawings and will herein be described in detail, with the understanding that the present disclosure is to be considered as exemplary of the principles of the invention and is not intended to limit the invention to the embodiment illustrated. The scope of the invention will be measured by the appended claims and their equivalents.

The optical and particle flow elements of a flow cytometry apparatus 10 are illustrated in FIG. 1. The optical and flow elements of FIG. 1 represent the major components of a flow cytometry apparatus for moving particles, such as cells or the like, in liquid streams, substantially one at a time, in order to determine their characteristics. For example, the elements of the apparatus of FIG. 1 may be included in a FACS fluorescence-activated cell sorter, manufactured and sold by Becton Dickinson Immunocytometry Systems, San Jose, Calif.

The FACS cell sorter analyzes and sorts cell populations on the basis of light scatter and fluorescence in a wide variety of research laboratory applications. In addition to the optical and flow elements to be described in more particular detail herein, and which may be embodied in an instrument such as the FACS cell sorter, other details of a cell sorting apparatus useful in conjunction with the present invention are described in U.S. Pat. No. 3,826,364 which is incorporated herein by reference. It is understood that the present invention is useful in many different types of flow cytometry apparatuses whether measuring light scatter, fluorescence, particle volume or other optical parameters for the identification or quantification of cells or the like in a sample liquid medium.

Excitation energy is provided in flow cytometry apparatus 10 by a beam of light 12 produced by light source 11. Beam 12 is produced by a laser, but an arc lamp such as a mercury or xenon arc lamp may also be used. It is preferred that light source 11 is a model Innova 90 laser from Coherent Radiation, Palo Alto, Calif. Light beam 12 is modulated by traveling wave modulator 13 to produce modulated beam 12a. Traveling wave modulator 13 is preferably a Model 3200 available from Crystal Technology, Mountain View, Calif.

Aperture and steering optics 14 and a focusing lens 15 are positioned in the optical path of the light beam 12a. Lens 15 focuses the modulated light beam 12a at liquid stream 16 containing the particles or cells under investigation. In the present flow cytometer apparatus aperture and steering optics 14 direct the modulated light beam 12a at flow chamber 17 which is positioned in the optical path after the lens 15 and aperture and steering optics 14. Flow chamber 17 is made of a material transparent to light of the same wavelength as that of beam 12a and to any fluorescent emissions of interest. Flow chamber 17 surrounds liquid flow stream 16. Lens 15 is used to obtain an adjustment of the focused light beam on the liquid stream.

As seen in FIG. 1, nozzle 18, incorporated within the flow cytometry apparatus of the present invention and preferably as a part of the flow chamber 17, facilitates the flowing of particles within liquid stream 16 through flow chamber 17. The utilization of nozzle 18 of this type is well-known and is described, for example, in U.S. Pat. No. 3,826,364. Nozzle 18 provides a hydrodynamically focused flow of particles within a sheath fluid, the sheath fluid and particles comprising liquid flow stream 16.

As each particle 43 passes through an adjusted focused light region in flow chamber 17, where light beam 12a intersects liquid stream 16, light is scattered and may be detected. Fluorescent particles will also emit fluorescence which may be detected.

As shown in FIG. 2, the modulating frequency for traveling wave modulator 13 is provided by frequency synthesizer 76 (Fluke Model 6160B) which generates a sine wave having a frequency between 10 MHZ and 100 MHz (preferably 30 MHz) and a power level of 13 dBM across a load of 50 ohms. The output of frequency synthesizer 76 is low pass filtered by low pass filter 89 (Allen Avionics, Inc., Model F4095, Mineola, N.Y., cut off frequency of 40 MHz for a frequency of 30 MHz) to minimize harmonic distortion due to the quality of the frequency synthesizer 76.

The low pass filtered signal is supplied to a biased tee 83. In the preferred embodiment, biased tee is a capacitor 83a of 0.1 µF which blocks the d.c. voltage from d.c. power supply 84 (Deltron, Inc., North Wales, Pa. W112A) thereby isolating frequency synthesizer 76. The d.c. voltage and the low pass filtered signal are summed at junction 83b and are sent to modulator driver 87. Modulator driver 87 (Crystal Technology 1200-10) generates a 200 MHz signal whose intensity is modulated output 83c of biased tee 83. The 200 MHz signal from modulator driver 87 produces modulated waves in traveling wave acoustic-optic modulator 13.

Fluorescence and wide angle light scatter are typically collected at 90° relative to the axis of light beam 12a. In FIG. 1, axis 24 represents the 90° viewing axis for the collection of fluorescence and wide angle scatter. Lenses 19 are placed across axis 24 to collect light passing along axis 24.

Modulated beam 12a is made up of sinusoidally modulated light waves having a modulation frequency in the range from 10 to 100 MHz. Beam 12a illuminates the cells 43 (See FIG. 1) passing through flow chamber 17. Light is scattered by each cell 43 as it is illuminated. Some of this scattered light 35 is reflected by dichroic mirror 25, filtered by filter 37 and detected by photomultiplier tube (PMT) 36. Fluorescence beam 31 is also emitted by each fluorescent cell. Some fluorescent light 31 passes through dichroic mirror 28 and is detected by PMT 39 after being filtered by filter 40.

As mentioned above, flow cytometer 10 measures phase fluorescence lifetimes by determining phase shift between a reference signal and a fluorescent emission from a particle or cell passing through its flow chamber 17. The reference signal is typically the light scattered from the particle by the modulated laser light 12a; alternately if the particles emit a second fluorescence signal that one wishes to use for the reference, then the reference signal is that fluorescence.

The choice of dichroic filter 40 depends on the wavelength of the fluorescence of interest emitted by the particles under investigation. For example, for cells stained with phycoerythrin-conjugated antibodies, a 585/42 nm band pass filter may be used (i.e., the peak of phycoerythrin fluorescence emission).

The selection of dichroic filter 37 depends on the wavelength of light to be used as a reference signal. For example, if the light scatter of the particle is to be used as a reference, and the excitation laser emits 488 nm light, then a 488/10 nm band pass filter may be used (i.e. the same wavelength as the laser, and consequently the scattered light). Alternatively, if the particles of interest emit fluorescence that one wishes to use for the reference signal, then dichroic filter 37 is chosen to transmit that fluorescence. For example, for cells stained with fluorescein-conjugated antibodies (in which it is desired to use the fluorescein fluorescence as a reference for some other fluorescence lifetime measurement), a 530/30 nm band pass filter may be used.

The selection of dichroic mirror 25 depends on the selection of both dichroic filters 37 and 40. The cutoff wavelength of the dichroic mirror is selected to be between the peak wavelengths of dichroic mirrors 37 and 40. For example, if dichroic filter 40 may be a 585/42 nm band pass filter, and dichroic filter 37 is a 48/10 nm band pass filter, then dichroic mirror 25 may be a 540 nm long pass filter.

Those skilled in the art will appreciate that various lenses, filters, barriers or the like may be employed in conjunction with each of the photo multiplier tubes to obtain as pure a signal as possible. Other photomultiplier tubes and detectors may also be present but are not material to the invention.

Figure 3A:
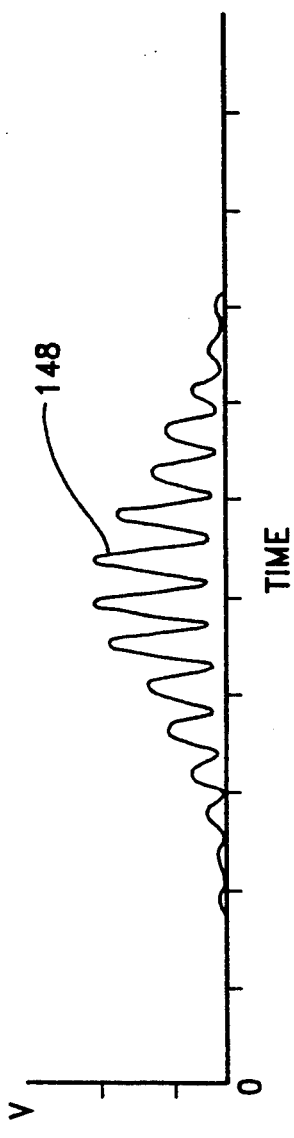

PMT 39 produces a current output which is proportional to the fluorescence emitted by the particle under consideration. This current is converted into a voltage by amplifier 147 (Comlinear Corp. CLC 167) having a voltage gain of about 10. The output 148 of amplifier 147 is represented in FIG. 3a. This output is split by power splitter 149 (Mini-Circuits, of New York, N.Y., Model ZFRSC 2050) which produces one signal which may be stored in a computer after being suitably conditioned and digitized. Output pulse 148 is made of an envelope produced by the fluorescence emitted as the particle passes through light beam 12a, modulated by modulator 13. The other signal 149f produced by power splitter 149 is conditioned by signal conditioning module 150.

Figure 3B:
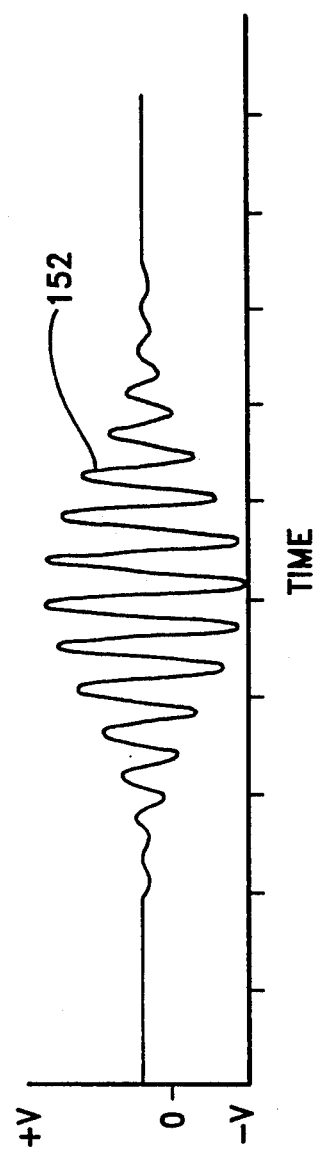
Figure 3C:
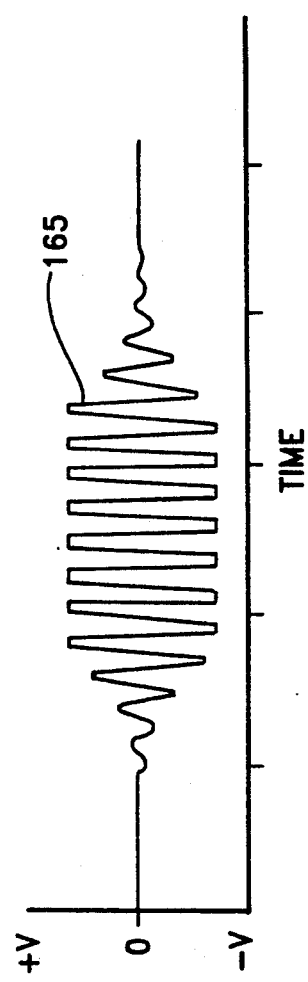

Signal conditioning module 150 performs the following operations:

Filter 151 (Allen Avionics Model F4086) band pass filters signal 149f so that it comprises substantially only frequencies in a range between 29 and 31 MHz in the preferred embodiment when the frequency of modulation of light beam 13a is 30 MHz. Band pass filtered pulse 152 is represented in FIG. 3b. Attenuator 153 attenuates the signal so that the amplitude of the pulses caused by particles of interest lies between −25dBm and 0dBm. Limiting circuit 155 (Avantek Milpitas, CA. Model 404−53) limits the filtered and attenuated signal eliminating amplitudes above −30 dBm such that the output signal has a level of 10 dBm. Amplitudes below −30 dBm are increased by 40 dBm. The limited signal 165 is shown in FIG. 3c. The limited signal is then band pass filtered by band pass filter 166 (Allen Avionics Model F4086) which removes the harmonics in the signal including those which may have been introduced by limiter 155. This signal 167 is substantially sinusoidal as shown in FIG. 3d. Finally, the signal is amplified by amplifier 168 (Mini-Circuits of New York, N.Y. model ZHL-6A/BNC CAT-20 with input attenuator) to 7 dBm for input into double balanced mixer 69.

The scattered signal 49s is conditioned in the same way by its own signal conditioning circuit 50. Band pass filter 51 corresponds to and is of the same type as band pass filter 151 and band pass filter 66 corresponds to band pass filter 166. Variable delay line 88 is interposed between attenuator 53 and limiter 55. Variable delay line 88 adjusts the phase of the scatter signal. It is necessary to adjust the phase in order to compensate for the length of transmission cables and variations in the performance of the system components. It is also necessary to compensate for the transit times of a signals through PMTs 36 and 39 which are a function of the voltages applied to the dynode chains of the PMT. The preferred variable delay line is an Allen Avionics VAR016, adjustable from 0 to 16 nanoseconds.

Signals 67 (fluorescence signal) and 167 (reference signal), having been conditioned can now be multiplied by double balanced mixer 69 (Watkins Johnson, Palo Alto, Calif. Model M-1). The output 71 of mixer 69 (shown in FIG. 3e) is indicative of the phase difference between the fluorescent light 35 and scattered light 35. This phase difference is indicative of the fluorescence lifetime of the particle under consideration.

Output signal 71 is fed into research amplifier (Ortec Systems Model 820) which amplifies and integrates phase signal 71, to produce envelope 75 shown in FIG. 3f. The amplitude of envelope 75 is proportional to the phase shift $\theta$ between the fluorescent light 31 and scattered light 35. This phase shift is a property of the particle under investigation and can be used to identify the particle.

What is claimed is:

1. A method of identifying a particle for use in a flow cytometer, the method comprising the steps of:
   providing a beam of light;
   intensity modulating the beam of light;
   passing the particle through the beam of intensity modulated light;
   collecting light from the particle for use as a reference;
   collecting fluorescence emitted by the particle;
   generating a first signal in response to the light collected as a reference and a second signal in response to the fluorescence collected; and
   determining the difference in phase between the first signal and the second signal.

2. The method of claim 1 further comprising the step of using the difference in phase to identify the article.

3. The method of claim 1 wherein the light collected for use as a reference is light scattered by the particle.

4. The method of claim 1 wherein the light collected for use as a reference is fluorescence emitted by the particle.

5. The method of claim 1 wherein the step of determining the difference in phase between the first signal and the second signal comprises the step of multiplying the first signal by the second signal.

6. The method of claim 1 further comprising the steps of filtering the first and second signals.

7. The method of claim 1 further comprising the steps of limiting the first and second signals.

8. The method of claim 1 wherein the step of intensity modulating is performed by means of a traveling wave modulator.

9. A flow cytometer comprising:
means for producing a light beam;
means for intensity modulating the light beam;
means for passing a fluorescently tagged particle through the modulated light beam such that light is the particle emits fluorescence on passing through the light beam;
first fluorescence detecting means for detecting the fluorescence and generating a fluorescence signal in response to the fluorescence;
means for determining the phase shift between the fluorescence light and the modulated light beam.

10. The flow cytometer of claim 9 further comprising means for detecting at least part of the scattered light and generating a scatter signal in response to the scattered light and wherein the means for determining the phase shift between the fluorescence and the modulated light beam comprises means for determining the phase shift between the scattered light and the fluorescence.

11. The flow cytometer of claim 9 further comprising:
second fluorescence detecting means for detecting fluorescence emitted by the particle; and
wherein the means for determining the phase shift comprises means for determining the phase shift between the fluorescence detected by the first fluorescence detecting means and the fluorescence detected by the second fluorescence detecting means.

12. The flow cytometer of claim 9 wherein the means for determining the phase shift between the fluorescence and the modulated light beam comprises a mixer.

13. The flow cytometer of claim 9 comprising means for filtering the fluorescence signal.

14. The flow cytometer of claim 9 comprising means for limiting the fluorescence signal.

15. The flow cytometer of claim 9 wherein the means for modulating is a traveling wave modulator.

* * * * *